United States Patent [19]

Scheicher

[11] 4,278,630
[45] Jul. 14, 1981

[54] METHOD FOR THE PREPARATION OF IMPLANTS, AND IMPLANTS

[76] Inventor: Hans Scheicher, Rondell Neuwittelsbach 4, 8000 München 19, Fed. Rep. of Germany

[21] Appl. No.: 629

[22] Filed: Jan. 2, 1979

[30] Foreign Application Priority Data

Dec. 31, 1977 [DE] Fed. Rep. of Germany ....... 2759214

[51] Int. Cl.³ .............................................. B29C 1/04
[52] U.S. Cl. ...................................... 264/60; 264/220; 264/221; 264/225
[58] Field of Search ...................... 264/19, 56, 60, 221, 264/313, 220, 225

[56] References Cited

U.S. PATENT DOCUMENTS

| 3,605,123 | 9/1971 | Hahn | 264/60 |
| 3,997,637 | 12/1976 | Rogers | 264/56 |
| 4,115,488 | 9/1978 | Colpitts | 264/19 |

OTHER PUBLICATIONS

Pernot et al., "New Glass Ceramic Material for Prosthetic Applications", *J. Material Science*, 14 (1979) pp. 1694–1706.

*Primary Examiner*—John Parrish
*Attorney, Agent, or Firm*—Sughrue, Rothwell, Mion, Zinn and Macpeak

[57] ABSTRACT

A method is disclosed for the preparation of implants, especially dental implants, from ceramic substances having in particular a porous surface which stimulates ingrowth of bone tissue.

11 Claims, 11 Drawing Figures

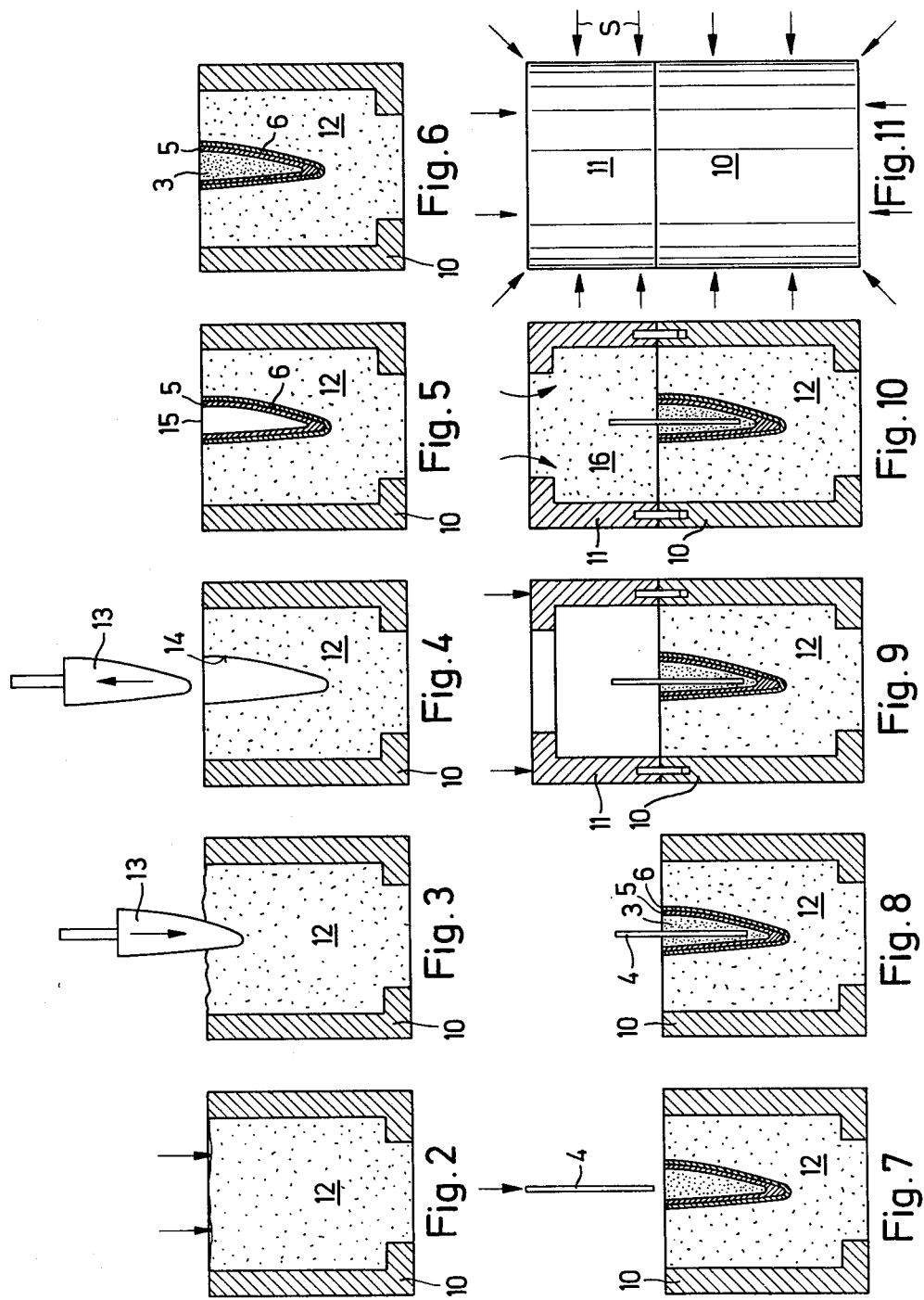

METHOD FOR THE PREPARATION OF IMPLANTS, AND IMPLANTS

DETAILED DESCRIPTION OF THE INVENTION

The present invention has as its object the suggestion of a method for the preparation of implants which is particularly simple and is feasible with conventional equipment available in dental laboratories, using conventional techniques and not involving additional expense pertaining to apparatus. This problem is solved according to the invention in that by introducing a model of the implant into a paste-like, high-temperature embedding substance, and leaving it in this until the embedding substance hardens, a negative mold of the implant is produced. After the removal of the model, the mold is lined via an opening reaching into its interior with a layer of a ceramic substance which should form the outer layer of the implant. The cavity of the mold is subsequently filled completely with dentine or core substances, and the opening is then sealed with a paste-like, high-temperature embedding substance. The embedding substance is allowed to dry and the whole is then heated to the sintering temperature of the ceramic substances used and the ceramic substances fired at this temperature for the usual time.

The equipment available in dental laboratories for the preparation of centrifugal castings suffices for carrying out the method according to the invention; the embedding substance is preferably introduced into a muffle or cuvette which is free of scale.

It is advantageous if the muffle is filled at first to about two thirds with the embedding substance previously stirred to a paste, the model subsequently pushed into the embedding substance from above, and, after hardening of same, pulled out again, and if after filling the negative mold with ceramic substance, the rest of the muffle is filled up with embedding substance.

It has proved favourable to prepare the negative mold using a wax model of the implant which is burned out after the embedding substance has hardened.

A variant of the method according to the invention is characterized in that a shell mold corresponding to the shape of the implant is lined via an opening reaching into the interior of said shell mold with a layer of a ceramic substance which should form the outer layer of the implant. The shell mold is subsequently filled completely with dentine or core substances, and the opening is then sealed with a paste-like, high-temperature embedding substance. The embedding substance is allowed to harden, and the whole is then heated to the sintering temperature of the ceramic substances used and the ceramic substances fired at this temperature for the usual time. The shell mold consists of a noble metal alloy (preferably platinum or a platinum alloy) which is not affected by a change of temperature and which is not destroyed at the firing temperatures of approx. 1000° to 1500° C.

The negative mold, or shell mold, is preferably filled by applying the ceramic substance, mixed to a paste with cocoa-butter or another conventional pasting agent, in layers. The outermost layer applied to the wall of the mold, or shell mold, which on firing provides the desired porosity, is applied to a thickness of 0.1 to 5 mm, preferably about 0.3 to about 1 mm. It can be fired prior to filling up the rest of the space in the mold with a dentine or core substance. The implant obtained by the method according to the invention is expediently treated after its removal from the embedding substance with a sandblast blower, at least in the region to be implanted, in order to guarantee complete opening of the vacuoles; in so doing the area which is not to be implanted can, if necessary, be covered, in particular with a wax or a plastic foil. In order to reinforce the interior structure of the implant, a metal or ceramic insert can be introduced, before covering the opening leading to the interior of the mold with embedding substance which has been mixed to a paste, into the interior of said mold, this being already covered, at least at the edge, or already partly or completely filled with ceramic substance. Aluminium oxide tubes or pins which protrude above the mold and later serve for fixation of the crown or other superstructure are especially suitable for this.

The ceramic substances used for the outer layer of the implant are characterized by a mixture of a ceramic base substance and fine inorganic fibers, whose melting temperature is higher than the sintering temperature of the ceramic base substance. When preparing ceramic substances according to the invention, care is taken that the ceramic base substance, in the molten form that it takes on during sintering, does not dissolve the fibers as such. By fine fibers, in this specification, fibers or filaments and wires having a diameter less than about 0.6 mm are meant.

The fibers according to the invention can be present in the ceramic base substance matrix in the form of whiskers, filaments, staple fibers, chopped fibers, threads, chopped strands as well as further processed products such as slubbings, rovings, netting, matting, fibrous webs, bonded fibrous materials, felts and woven materials. Usually, that is, if no extreme reinforcement effect is required, it suffices to have the fibers in short pieces, of lengths approximately 0.1–60 mm, preferably about 0.5–30 mm, in the ceramic base substance.

For the production of porous ceramic bodies, fibers in pieces of about 0.5–about 3 mm are particularly suitable. An adequately uniform distribution of the fibers in the base substances is generally sufficient to ensure that the ceramics manufactured from the substances have the desired rigidity. This applies especially for the production of porous ceramic bodies having surfaces not prone to rejection by the tissues and which enable adherence and ingrowth of bone tissue. These porous bodies contain a large number of vesicular cavities merging partly into one another like a sponge. The pores vary in diameter from the smallest pore of diameter less than 1 $\mu$m to pores with a diameter of over 500 $\mu$m, whereby in one piece of ceramic, pores of different sizes are evident. Pores of diameter from about 10 $\mu$m to about 400 $\mu$m are preferred. The average value of the pore diameter should be approximately 100–200 $\mu$m, whilst the quantity of pores having a diameter larger than 300 $\mu$m should not account for more than 10%, preferably 5%. In the porous bodies the pores take up a volume of about 10% to about 90% with respect to the total volume. Proportions of pores from about 20 Vol.% to about 30 Vol.% are especially suited for use as adhering layer for the ingrowth of tissue.

Conventional organic fibers prove unsuitable for the production of the substances according to the invention since their melting points are lower than the temperatures necessary for the sintering together of the ceramic base substances, the temperatures for the ceramic base substances used lying in a region from about 650°–1900° C. The composition of the ceramic base substances used within the framework of the invention at hand will be subsequently dealt with in more detail.

In the following, a series of fibers are indicated, though not claiming entirety, which are suitable for the manufacture of ceramic substances as according to the invention. They are as follows:

Pure quartz fibers from 99.99% silicon dioxide, which on account of their high thermal and chemical stability, present no problems when used for implants.

Carbon fibers, which in the purest form are referred to as graphite fibers, are relatively economical to manufacture. When using carbon fibers it must be remembered that although they present no physiological problems, the material exhibits a high heat conduction capacity and a high electricity conduction capacity. The processing of carbon fibers should be carried out in a vacuum in order to prevent oxidation.

Metal filaments, manufactured by heat-drawing with or without sheathing and by pressing out of the melt through narrow nozzle openings and subsequent solidification, or by the so-called Taylor Process. Metal filaments with a diameter equal to or larger than 100 $\mu$m can, according to DIN 60001 E, be referred to as wires. When metal filaments or wires make up the fiber content in the ceramic substances according to the invention and these substances are used for implants, care should be taken to use a ceramic base substance which, when molten, wets the metal filaments well, so that after solidification of the ceramic substance these are, if possible, not bare. Otherwise they could be attacked by the body fluids, which dissolve the metals and could lead to so-called "metallosis" i.e. poisoning by metal ions. The danger of such a metallosis is not great even if the metal filaments are not completely covered by the ceramic base substance, since the fibers account for only a small percentage of the total material and are furthermore embedded for the most part in the matrix of the ceramic base substance. Since however these are other fibers where the danger of metallosis can from the start be excluded, ceramic substances containing metal filaments as fiber content are generally not used for the outer layer of prosthetic elements but rather as reinforced core substances, these being covered by the overlying layers. Examples of metal fibers would be steel fibers, fibers of René 41 (a nickel-based alloy), niobium fibers, molybdenum fibers and tungsten fibers.

Filaments with a tungsten core, that is, reinforcing elements which are manufactured by making the actual reinforcing material on a tungsten core of, for example, about 12 $\mu$m. To these belong in particular boron threads, (diameter approximately 90–150 $\mu$m) which can be additionally coated with silicon carbide to a thickness of about 4 $\mu$m, or whose surface is treated with a nitration. Boron carbide filaments with a tungsten core, silicon carbide filaments (diameter approximately 10 $\mu$m) with a tungsten core and titanium diboride filaments with a tungsten core also belong to this group. A disadvantage of the last-mentioned threads lies in that they are relatively thick.

Synthetic ceramic fibers: i.e. synthetic fibers of borides, carbides, nitrides, oxides, silicides and/or silicates.

To these belong in particular: boron carbide fibers, boron nitride fibers and zirconium silicate fibers, which are very fine, as well as the coarser zirconium dioxide fibers and in particular the somewhat thicker aluminium oxide fibers; also the so-called Mullit fibers which comprise for the most part aluminium oxide. The ceramic fibers, as opposed to the metal fibers, have the advantage that when using the ceramic substances according to the invention for the preparation of prosthetic elements, there is no danger of metallosis or electrolytic disturbances. Basalt and kaolin fibers are also suitable (Kaolin fibers are preferably of thickness from about 1 $\mu$m to about 6 $\mu$m).

Details concerning the manufacture and the properties of the above-described fibers can be taken from a brochure on "Faserverstärkte Hochleistungs-Verbundwerkstoffe" by Rainer Taprogge, Rolf Scharwächter, Peter Hahnel, Hans-Joachim Müller and Peter Steinmann, of the Institut zur Erforschung technologischer Entwicklungslinien ITE.

A further group of fibers which is particularly suitable for the manufacture of the ceramic substances according to the invention are the so-called whiskers. Whiskers are discontinuous fiber-like single crystals with exceptionally high tensile strength and modulus of elasticity, which however are at present relatively expensive. But since only small quantities of the whiskers are required for the ceramic substances according to the invention their use is also economically feasible. Whiskers suitable for the ceramic substances according to the invention include in particular beryllium oxide whisker, boron carbide whisker, graphite whisker, magnesium oxide whisker, aluminum nitride whisker, silicon nitride whisker as well as in particular aluminum oxide—that is, sapphire whisker and silicon carbide whisker. Silicon carbide whiskers occur in two modifications, the so-called $\alpha$-silicon carbide whisker and the so-called $\beta$-silicon carbide whisker. The $\alpha$-silicon carbide whiskers are hexagonally-centered, in diameter about 10 $\mu$m to about 100 $\mu$m, and in length about 1 to about 60 mm. The $\beta$-silicon carbide whiskers are cubic, having diameters of about 0.5 $\mu$m to about 3 $\mu$m, and lengths of about 1 to about 30 mm. Precisely, these $\beta$-silicon carbide whiskers are excellently suited for embedding in dental ceramic base substances. Besides the above-mentioned whiskers, metallic whiskers such as, for example, chrome whiskers, iron whiskers, cobalt whiskers and nickel whiskers, conditionally also copper- and silver whiskers, can also be used in ways according to the invention. The same applies also for the so-called Schladitz whiskers, these being polycrystalline metallic threads. The above-mentioned metallic whiskers are all likewise subject to the disadvantage already mentioned in connection with metal filaments, namely that when not completely covered by the matrix of the ceramic base substance they can, on coming into contact with body liquids, be the source of possible metallosis and electrolytic disturbances, if the ceramic substances produced from them and the corresponding base substances are used for implants.

Details concerning the above-mentioned whiskers, expecially as to their manufacture and their properties, can be taken from the previously-mentioned brochure on "Faserverstärkte Hochleistungs-Verbundwerkstoffe". With respect to the silicon carbide whiskers attention is drawn also to an article by A. Lipp in the journal "Feinwerktechnik" 74, 1970, issue number 4, pages 150–154. Details concerning polycrystalline metallic whiskers or metallic threads can be taken from articles by Hermann J. Schladitz, published in "Fachberichte für Oberflächentechnik" 8. 1970, issue number 7,8, pages 145–150 and "Zeitschrift für Metallkunde" Band 59/1968, issue number 1, pages 18–22.

Generally one always uses one type of fiber in one ceramic base substance. In principle, however, also mixtures of different fibers can be used in one ceramic base substance.

As base substances, which are mixed with the above-mentioned fibers together with the ceramic substances according to the invention, conventional ceramic substances intended as bone substitute, particularly glass-ceramic materials, the familiar dental-ceramic substances and hard ceramic, as well as aluminium oxide ceramic substances and aluminium phosphate can be used.

As base substances one can be used in particular so-called core substances, i.e. porcelain substances which are used in a conventional way for the inner makeup of artificial teeth, and so-called dentine substances i.e porcelains which should replace the dentine in the natural tooth. One can however also use the so-called enamel substances, these serving as enamel layer for artificial teeth and porcelain crowns. So far as the base substances—this applies for core—and dentine substances—are normal dental-ceramic substances, they contain mixtures of quarz, kaolin, and feldspar. Typical examples of such base substances contain 70-90 parts by weight feldspar, especially orthoclase-(potassium)-feldspar, about 0.5 to 15 parts by weight—preferably 1 to 10 parts by weight—kaolin, and about 0.5 to 25 parts by weight—preferably about 1 to 18 parts by wt.—quarz, as well as about 0 to 2 parts by wt.—preferably 0 to 1.3 parts by wt.—pigments and opaques. Instead of the quarz, various allotropic silicon compounds such as, for example, cristobalite, can be used, this serving in particular to regulate the thermal coefficient of expansion. An increase in the proportion of silicon increases the power of resistance. Other base substances contain in place of the feldspar, nepheline syenite, a mineral made up of approximately 50% sodium feldspar, (albite) 25% potassium feldspar (microlite), and 25% nephelite. In the case of the dentine substances, the silicon content can be raised to about 20 parts by wt. In the base substances the silicon content can be wholly or partly replaced by aluminium oxide. If the aluminium oxide content is raised, for example to 60 and 70 parts by wet., then base substances are obtained which can be classified with the familiar hard-porcelains and can also be referred to as aluminium oxide ceramic substances.

The base substances can further contain various fluxes, such as, for example, lithium and potassium silicate, which effect alterations in the firing temperature or the thermal coefficient of expansion. The addition of a flux enables adaptation of the base substances to the thermal coefficient of expansion of metals or hard ceramics, so that these base substances can be fired onto profile parts, cores, inserts or superstructures of these materials. One differentiates accordingly between metal-ceramic and hard-ceramic substances. As examples of aluminium oxide ceramic substances, i.e. of ceramic substances which can be fired onto $Al_2O_3$ cores, the Vitadur and Vitadur-S-ceramic substances can be mentioned, which are available as core substances, dentine substances and as enamel substances, and which are manufactured by the Vita Zahnfabrik Säckingen in West Germany. Relevant details can be taken from the brochure "Die Vitadur-Technik" Nr. 11/73-500 of the Vita Zahnfabrik, Säckingen-Germany.

Examples of metal ceramic substances are described in the DT-AS No. 1 441 346, to which reference is here made. As further examples of metal-ceramic substances the Biodent-dentine and the Biodent core substances of the firm De Trey Gesellschaft D 6200 Wiesbaden as well as the Vita-VMK substances of the Vita Zahnfabrik, Säckingen, Germany and the Vivodent-PE-ceramic substances of the firm Ivoclar AG FL-9494 Schaan/-Liechtenstein can be mentioned.

An example of a metal-ceramic base substance sintering at a firing temperature of 900° C. has the following composition:

| Component | Percent | Component | Percent |
|-----------|---------|-----------|---------|
| $SiO_2$ | 65,518 | $Li_2O$ | 1,236 |
| $Al_2O_3$ | 14,078 | CaO | 1,778 |
| $K_2O$ | 9,552 | MgO | 1,202 |
| $Na_2O$ | 6,636 | | |

Examples of glass ceramic base substances are the pyrex glass from the GCC Company in Japan and Vycor glass from the Dentists Supply Company in the USA.

The DT-AS No. 2 326 100 describes a glass ceramic base substance with apatite crystal phase, which can likewise be used for the manufacture of substances according to the invention.

The DT-OS No. 2 238 263 describes a further example for ceramic base substances.

The above-mentioned ceramic substances are for the most part not porcelains according to the classical description—i.e. not mixtures of quarz, feldspar and Kaolin, but porcelain products attaining to a different concept which, with respect to their composition, molding and firing do not resemble normal porcelain in any way. With regard to this terminology attention is drawn in particular to an article by Dr. Walter Pralow, Säckingen, in the journal "Das Dental Labor", issue number 2/1969, pages 66 et seq. The adoption of the expression "Ceramic substances" for these substances too arises from the fact that these substances are prepared according to ceramic methods, although as far as their composition is concerned, they resemble more the glasses.

Substances are preferably used whose firing temperatures lie in the region of 900° to 1400° C., preferably 900°-1200° C. The melting temperatures of the threads must be higher than the sintering temperature of the base substances used in conjunction with them, this temperature difference amounting to some thousand degrees Celsius, for example to about 3100° C. The temperature differences are preferably 400° C. or more.

The fibers used are preferably of lengths from about 0.1 to 60 mm, whereby lengths from about 0.5 mm to about 30 mm are particularly preferred. Fibers of lengths from 0.5 mm to about 3 mm are particularly suitable for the production of porous bodies, preferably for the dental field.

The thickness of the fibers employed reaches as a maximum to about 600 $\mu$m, whereby fibers of thickness from about 0.5 $\mu$m to about 100 $\mu$m are preferred. For the preparation of dental ceramic substances which are applied as the outer layer on implants, whiskers of thickness from about 0.5 $\mu$m to about 20 $\mu$m have proved suitable, thicknesses to about 10 $\mu$m being especially favorable. The best results to date were obtained with $\beta$-silicon carbide whiskers, these having a thickness of about 0.6 to 3 $\mu$m.

Very good results were obtained with basalt threads of thickness about 6 $\mu$m and lengths about 1-3 mm, and carbon fibers with a thickness of about 10 μm and lengths from about 0.5 mm to about 1.5 mm.

For the formation of a layer permeated by vacuoles, on the other hand, this enabling an easier ingrowth of bone substance, relatively small additions of fibers to the ceramic base substances suffice.

Experiments have shown that a fiber Vol.% of 0.005 to 0.02 relative to the ceramic base substance in unprocessed powder condition can be adequate.

For the formation of the layer permeated by vacuoles, use of fibers with up to 5 wt.%, preferably approx. 0.002 to about 0.05 wt.%,—relative to the weight of the ceramic base substance in not-yet-processed powder form—gives excellent results.

In a special modification the ceramic substances contain an admixture of approx. 1-20 wt.%, preferably about 2 to about 5 wt.%, relative to the total substance, of very finely divided metallic silver. These silver-containing ceramic substances are used preferably in the case of enossal implants at those points where the implants extrude from the body tissues, i.e. at those points where there is an increased risk of infection. With artificial teeth this is the region where the dental root extrudes from the jaw bone into the mouth cavity. Here for example, the silver-containing ceramic substance is applied as an approx. 2 mm wide ring to the artificial dental root, so that the substance, on account of the anti-bacterial effect of the silver, serves as a barrier against introduction of bacteria in the jaw region.

Introduction of the very finely-divided metallic silver into the ceramic substance can be effected as follows: To any one of the above-described ceramic base substances—preferably a dentine substance such as, for example, a Vitadur-dentine substance—a silver salt having anions easily decomposed by heat or an easily reducible silver salt is added in quantities from about 1 to about 50 wt.%, preferably about 5 to about 30 wt.% relative to the ceramic base substance, and is uniformly mixed with the ceramic base substance, the salts preferably being in solution.

Silver salts from organic acids are especially suitable, as for example silver oxalate, silver acetate, and silver tartrate. Also silver nitricum, i.e. silver nitrate, is suitable here. The silver salts mixed with the base substances are subsequently decomposed. This is possible by warming above the relevant decomposition temperature. With this procedure however great care must be taken since—as for example with silver nitrate—poisonous fumes can result which must be very carefully led off. In order to avoid endangering the personnel with fumes of this sort the decomposition is accordingly carried out preferably by a chemical reduction. The mixture of silver salts and base substances is hereby mixed with a reducing agent, as they are used for example in photography, being referred to as "Developer". Examples of such reducing agents or developers are androquinone, hydroquinone, pyrocatechin, ortho- and meta-amino phenols, such as metol (para-n-methaminophenol); glycin (4-hydroxy-phenyl-amino acetic acid); phenidon (1-phenyl-pyracolidon 3) hydrazine; hydrophosphorous acid $H_3PO_2$; dithionate ($Na_2S_2O_4$) as well as in particular formalin, aldehydes such as formaldehyde, acetaldehyde, propionaldehyde and also ascorbic acid and glucose. By stirring the mixture of the relevant ceramic substance and the relevant silver salt to a paste with the solution of such a developer, metallic silver is made to precipitate out from the silver salt. The product is subsequently washed several times with distilled water.

When using formalin, acetalhyde, propionaldehyde, ascorbic acid and glucose as reducing agent the repeated washing can be omitted due to their good compatibility under different conditions. The product is then dried and ground in a mortar, after which it can as ceramic base substance be further processed—as described before—and with fibers mixed into it or not.

In the following an example is cited for the introduction of very finely-divided metallic silver into a base substance:

1 g of silver nitrate and 10 ml of distilled water are introduced into a 100 ml flask. Through shaking the silver nitrate is dissolved. Then 10 g of a Vitadur-dentine base substance are added, as well as 20 ml or a normal commercial hydroquinone developer. The mixture is shaken carefully. The flask is subsequently filled with distilled water and the product allowed to settle. The liquid is then decanted, and the residue washed by repeated filling with, shaking and decanting of distilled water. The solid matter at the bottom of the flask is then dried. The dried product is ground in a mortar. It can then be further processed, as previously described.

The ceramic substances according to the invention can, according to the requirements in each case, be mixed afresh with the fibers and a corresponding base substance by the technician responsible. In this case it is advantageous if the fibers can be supplied in packaged quantities.

In many cases however it is preferable if the ceramic substances are provided already mixed, and need only be opened and fired. With a number of fibers which don't exhibit any large surface energies and don't have a tendency to form bundles, it is sufficient to mix the fibers of the corresponding lengths and thicknesses with the relevant quantity of powdered ceramic base substance. In the case of other fibers however, this is not always possible, since these, on account of large surface energies, are held together in balls or bundles, this making a uniform mixing with the ceramic base substances difficult. This is the case particularly with, for example, basalt fibers and whiskers, whereby especially with β-silicon carbide whiskers separation problems occur. In these cases the fibers are brought into contact with a liquid or solid medium becoming volatile below the sintering temperature of the ceramic base substances, this medium exhibiting a surface energy which enables or effects separation of the fibers. For this such media are preferably used which solidify at room temperature and which are liquid at somewhat higher temperatures. The separation of the fibers occurs through the fibers being mixed with the liquid or liquefied medium. Examples of such media suited for the separation of fibers are synthetic materials, synthetic resins, waxes and glycerine, or cocoa butter, which have proved successful particularly for the separation of β-silicon carbide whiskers, basalt fibers and carbon fibers.

The ceramic base substances can be stirred into the liquefied medium either after this, or just immediately before the processing of the ceramic substances, for which purpose the medium bringing about the separation is warmed again above its solidification point. When cocoa butter is used for separation of the fibers and kneading of the ceramic substances, it is added in quantities of about 10-100 wt.%, preferably about 40-80 wt.% relative to the ceramic substances of fibers and base substances as according to the invention.

It is particularly useful to decant the ceramic substances after their preparation into small containers, for example in mixing capsules, and to let them solidify in these. For the processing of the ceramic substances, the same are then warmed up in their containers so that they can be applied directly from these and processed. When the ceramic substances are prepared by means of a single mixture of the base substances with fibers having no tendency form bundles, they are further processed as follows:

The ceramic substances are mixed to a paste with a modelling liquid which can be the same one as employed for mixing the ceramics used as base substances. The quantity of the modelling- or respectively mixing liquid amounts to about 5–10 wt.% to the quantity of the ceramic substance. Possible excesses of the mixing liquid are drawn off, for example by means of blotting paper. Distilled water is particularly suitable as a mixing liquid. Subsequently the dough-like ceramic substances are introduced into a mold, or compression mold, whose shape corresponds to that desired for the end product after the firing, for example a dental implant or a bone implant. Through shaking or such methods the ceramic substances are adequately consolidated, preventing the appearance of undesired large cavities during the firing and ensuring that the model is in each case perfectly shaped. The ceramic substances can also be fired onto a substrate. In this case they are applied in the desired layer thickness.

If the ceramic substances according to the invention contain fibers with a tendency to form bundles and are mixed with the corresponding base substances by means of the previously described volatile medium exhibiting a high surface energy, or if non-bundle-forming fibers are mixed with these media, preferably with cocoa butter which is preferred since this cocoa butter, on heating, doesn't boil but just sublimes directly, then before introducing the mass into the mold or applying onto a substrate it must be heated above the melting point of the medium.

When firing so-prepared ceramic substances according to the invention a muffle furnace or another corresponding furnace or a hot press containing the ceramic substances according to the invention is heated firstly to a temperature lower than the sintering temperature of the base substances used in the ceramic substances but which however is high enough to cause the medium bringing about a separation of the fibers, or the mixing fluid, to evaporate or sublime. This temperature is preferably selected to lie between about 400° C. and about 600° C., usually about 500° C. This temperature is maintained long enough to confirm that the mixing liquid or the medium bringing about a separation of the fibers has completely evaporated or sublimed. This can be determined for the individual media by simple experiments, whereby one carries out the procedure over varying time intervals, letting the substances subsequently become cold and then determining the proportion of the medium by analysis. This pre-firing takes as a rule about half an hour. After this the temperature in the furnace is raised to the firing temperature of the base substances used in the ceramic substances in each case. These temperatures are in the case of normal commercial ceramic substances, which are as a rule used for the base substances, in each case indicated. In the case of other base substances they are determined by simple experimental series, whereby the firing temperature for different samples is raised step-wise by a few degrees Celsius.

When the desired temperature in the interior of the ceramic substances according to the invention has been reached, this temperature is maintained for the normal firing time for firing of the corresponding base substances—i.e. for time intervals ranging between 2 and about 30 minutes, preferably about 6 to about 10 minutes. After a further quarter of an hour the furnace is opened and the fired substance in the mold is removed, if necessary after a further cooling period in the furnace. Particular advantages are evident from the use of ceramic substances according to the invention when these are fired as an outer layer onto the implant, forming respectively a periosteum—or dental periosteum substitute. The ceramic base substance can here be either a core substance, a dentine substance or an enamel substance, its specific composition being dependant on whether the implant is to be made as metal-ceramic or as hard-ceramic.

The implants exhibit in this case, from the outside to the inside, the following layering possibilities:

(a) dentine substance with fibers fired on a core substance without fibers.

(b) dentine substance with fibers fired on a dentine substance without fibers, which in turn in given cases is fired on a core substance.

(c) core substance with fibers, fired on a core substance without fibers.

(d) enamel substance with fibers, fired on a dentine substance and/or a core substance without fibers.

When the ceramic substances according to the invention form the outermost layer of a bone or dental root implant as bone periosteum- or dental root periosteum substitute, it is applied expediently in thicknesses of about 0.1 mm to about 5 mm, preferably in thicknesses of about 0.1 mm to about 1 mm. For dental implants the optimal thickness is about 0.3 mm to 0.5 mm. The desired vacuoles in this layer, which allow for the ingrowth of tissue, are formed during firing of the ceramic substances according to the invention, provided this doesn't occur under high pressure—i.e. in a vacuum (about 5–50 mm Hg, preferably 10–20 mm Hg,) under atmospheric pressure and with small excess pressures.

Examples for possibilities of carrying out the repressing are described in No. P 27 11 219.2. With higher proportions of fibers pressures higher than 1 kp/cm$^2$ are necessary in order to avoid the pores of the fired product becoming too large and the product brittle. If the fibers are metallic fibers, the firing is carried out in a vacuum or in thre presence of a protective gas in order to prevent oxidation. As protective gases the noble gases are particularly suitable i.e. Helium, Argon, Krypton and Xenon, Argon being here the most preferred. If the firing occurs in sealed containers however, this precauting can, possibly be dispensed with. The size and number of the vacuoles, that is the porosity of the periosteum substitute layer produced from the ceramic substance according to the invention, can be regulated through the respective addition of fibers to the ceramic base substance.

The most suitable mixtures within the given values can be determined for the individual fibers by simple experiments. When the vacuoles measure about 10 μm in diameter to about 300 μm in diameter and/or in depth, a good ingrowth into the implant in the bone tissue is to be expected, i.e. the new-forming bone tissue grows into the vacuoles and creates a firm contact between bone and implant. One can observe this from X-Rays taken at time-intervals of several weeks. The previously-given values are to be understood as average values. Besides the vacuoles of the given size a large number of small and very small vacuoles can be in evidence. Also the existence of single somewhat large vacuoles doesn't matter.

It is particularly useful if the previously-described ceramic substances intended for the outer layer of the implant contain additional substances stimulating bone formation and/or bone growth, especially tricalcium phosphate and tertiary calcium phosphate.

Substances further suitable for stimulating bone formation and/or bone growth are in particular sodium, lithium, carbon, magnesium, boron, fluorine, silicon, phosphorus, calcium, potassium and/or yttrium ions, and/or ions of the rare earths, these substances being added in body soluble form. Sodium, calcium, boron and phosphorus ions are particularly favourable. The suitability of these previously-known ions for stimulating the growth of bone tissue onto vitrified aluminium oxide ceramic is known from the DT-AS No. 23 24 867.

In order to stimulate ingrowth into the implant it is preferable to introduce powdered apatite crystals—e.g. ground in a mortar—, which are known to strongly accelerate bone regeneration, into the ceramic substances intended for the outer layer of the implant. Besides natural bone apatites, apatites being isomorphic to hydroxylapatite seem especially suitable, in particular very small calcium phosphate hydroxylapatite crystals. The addition involves about 5 to 70 wt.%, preferably about 10–30 wt.% relative to the dry content of the ceramic substances. Further substances stimulating bone growth are described in the DT-OS No. 26 06 540. When ground to a powder they can serve as the additive mentioned.

An addition of denatured bone meal is also possible. The addition expediently involves about 2.5 wt.% to about 70 wt.%, preferably about 5 wt.% to about 20 wt.% relative to the dry content of the ceramic substance.

In the following, an example for the manufacture of denatured bone meal is given:

Calves' vertebrae are dried at 100° C. for 8 hours. The dried bones are coarsely ground and subsequently freed from fat by leaving in ether for 24 hours. After drying off the ether the bone meal is left 24 hours in 20% hydrogen peroxide and then boiled for 10 minutes in same. The hydrogen peroxide is then poured off and the material subsequently dried. The powder obtained in this way from macerated bones is ground very finely in a mortar (this procedure is based on work by R. and A. Baumeister—see J. Bone Surg. 39 A 153 (1957)).

The outermost layer of the implants thus preferably contain an addition of substances stimulating bone formation and/or bone growth, which is added to the ceramic substances before these are mixed to a paste. Particularly useful here is apatite in powder form, especially calcium phosphate hydroxyl apatite in quantities of about 5 to 70 wt.%, preferably about 10 to 30 wt.% relative to the dry content of the ceramic substances. In the following an example is given for the preparation of implants following the method according to the invention.

FIGS. 2 to 11 show schematically the individual steps of an embodiment of the preparatory procedure.

Figure 1:
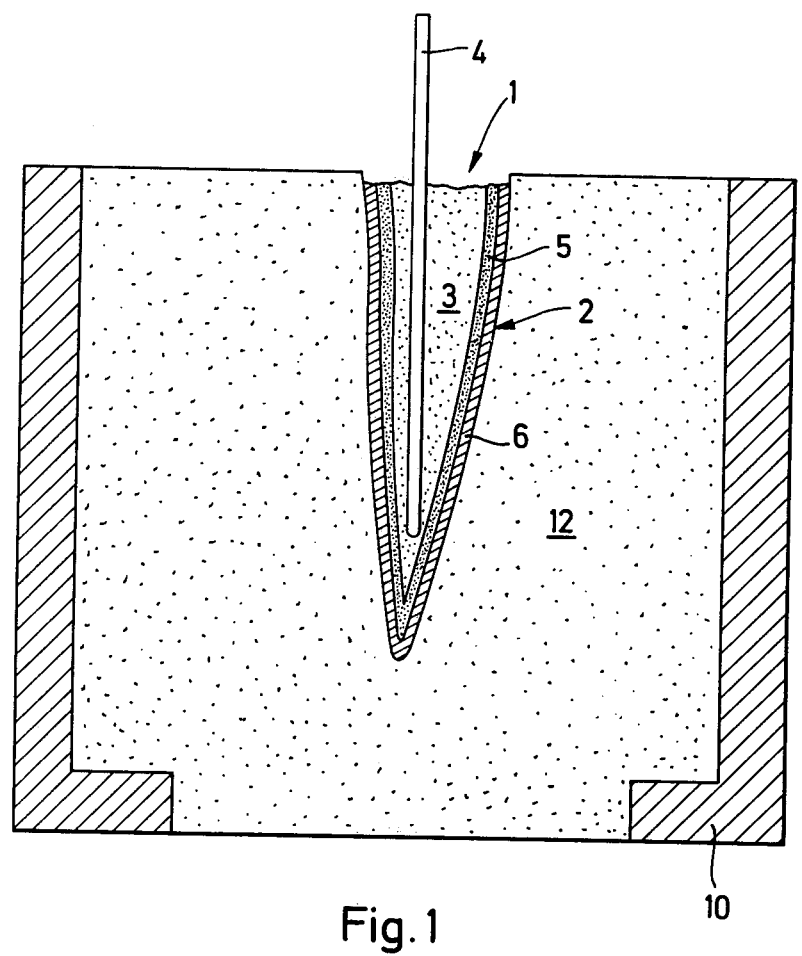
FIG. 1 shows, in the interior of a cuvette and in longitudinal section, a dental root substitute to be implanted.

The procedures shown in FIGS. 2 to 11 are primarily intended for the preparation of implants which reproduce the extracted teeth or the extracted roots true to shape. These implants should, in the root region, be provided with a porous coating layer having a large number of vacuoles enabling tissue ingrowth and thus rigid support of the implant.

The implants are made up of different layers, surrounding one another, in a manner similar to the dental prosthetic elements prepared by conventional porcelain-press techniques or metal ceramic techniques.

FIG. 1 shows, in the interior of a cuvette, which in connection with its method of preparation will be dealt with more closely later, a tooth root substitute 1 in longitudinal section. The tooth root substitute 1 consists in the root region 2, seen from the interior to the exterior, of a core substance 3, in which a reinforcement element 4 is when necessary embedded. The core substance 3 is surrounded layerwise on the outside by a dentine substance 5, which in turn is surrounded by a layer 6 of special porous ceramic substance. The layer 6 consists likewise of a dentine substance or core substance which is mixed with thin inorganic fibers whose melting point is considerably higher than the temperature at which the materials making up the artificial tooth 1 are sintered. The layer 6, measuring preferably about 0.3 mm–0.5 mm in thickness is, as already frequently described, permeated by a large number of vacuoles, these allowing ingrowth of bone tissue when the root region 2a is implanted in an artificial or natural tooth alveolus of the jaw.

Layers 3 and 5 can, as a variation from the previous example, also consist of a dentine, a core substance or aluminium phosphate.

In the example illustrated it is assumed that the dentine substance in layer 5 and 6 is the same. For this reason the dividing line represented in the figure between these layers is, in a section through a real artificial tooth or a dental root substitute, only apparant in that within the dividing line there are no fibers, meaning that at the dividing line the porosity, or the depth of the vacuole-permeated outer layer, essentially ends.

The dental root substitute 1 can be made from metal-ceramic substances or from hard-porcelain substances, or from Vitadur- or Vitadur-S-substances, whereby corresponding core substances, corresponding dentine substances—also in layer 6—are used. In the case of metal—ceramic substances the reinforcement element 4 consists of metal.

As metals in questions here one can use, among other special alloys used in metal ceramics, gold alloys with a high platinum content, which for the purpose of increased hardness contain iron and other elements and melt at temperatures of about 1100°–1200° C. Also palladium alloys, hardened with ruthenium, with small amounts of gold or silver, which melt between about 1450° C. and 1600° C., as well as the so-called Feram alloys of cobalt-chrome from the Niranium Corporation Long Island, and D.J. metal with nickel as base material of the Durailium Products Co. Chicago. The DT-OS No. 25 14 672 describes further suitable alloys. Further examples of such alloys are known under the marks Degudent and Degucast, these being gold-ceramic and being manufactured by the firm Degussa GB Dental- und Goldhalbzeug D 6000 Frankfurt. Further gold-ceramics are known under the marks Herador (Firm Heraeus, V. 4, V. 44) (Firm Métaux Précieux) Degudent Swiss (Firm Cendress & Métaux) (Armator II) (Firm Usine Genevoise Degrossissage d'or) Williams Gold, Ceramco Gold and Stern Gold. From among the precious metal refined alloys are mentioned in particular Wiron S and Wiron, which have a composition on the basis of nickel-chrome and are manufactured by the firm Bremer Goldschlägerei Wilhm. Herbst 2800 Bremen 41.

In the case of hard-ceramic substances the reinforcement element 4 is a prefabricated hard ceramic element, preferably a small hard-ceramic bar, tube or sheet, preferably of aluminium oxide.

In the following the method of preparation of the dental root substitute will be dealt with in more detail. FIG. 2 shows how a cuvette half 10 is levelles filled with a high-temp embedding substance 12 which has been mixed to a paste. The embedding substance should if possible have a small thermal coefficient of expansion. Examples of embedding substances are special substances such as Deguvest from the firm Degussa GB Dental-und Goldhalbzeug D 6000 Frankfurt 1, Wirovest from the firm Bego, Bremer Goldschlägerei, Wilh. Herbst, 2800 Bremen 41, Emil-Sommer-Str. 7, Neo-Brillat from the firm Dentalchemie C. C. Schrepfer, Marburg/Lahn, Germany, Aurovest or Aurovest B, a quarz embedding substance from the firm Bego, Bremer Goldschlägerei, Wilh. Herbst and Hüdrovest from the firm Frankonia in West-Germany.

In the embedding substance 12 of the lower cuvette half, before it hardens, a wax model 13, true to the original is embedded with the labial or lingual side down as shown in FIG. 3.

The wax model 13 is left in the embedding substance 12 until this is hard. It is then pulled out again, as shown in FIG. 4, so that a negative mold 14 is formed which is true to shape.

When the embedding substance is completely dry the ceramic substance, mixed to a paste, of layer 6 is first applied via the upper opening 15 of the mold, using a brush, spatula or something similar. When this in turn is dry, the adjacent layer 5 is applied. This stage is shown in FIG. 5. Subsequently, the cavity remaining in the interior of layers 5 and 6 is filled with core substance 3; this is also done preferably in layers. The end result is shown in FIG. 6.

To reinforce the dental root substitute 1 a reinforcement element 4 is introduced into the core substance 3. FIG. 7 shows this process, FIG. 8 the end result. Subsequently an upper cuvette half 11 is positioned on top of the lower cuvette half; the upper half is connected to the lower one e.g. by means of pins which slide into holes, not shown in more detail, in the lower cuvette. The cuvette halves are connected such that the high pressure at sintering does not cause the two cuvette halves to be pushed against one another. Positioning of the upper cuvette on the lower one is shown in FIG. 9. The space above the hardened embedding substance 12 and the mold 14 filled with ceramic substances is subsequently filled completely with further embedding substance 16, mixed to a paste, as is shown in FIG. 10. When the embedding substance 16 is dry the cuvette formed from the halves 10 and 11 is put into a furnace, is sintered there by means of heat radiating from a heat source in the direction of arrow S, and is fired as previously described. The finished dental root substitute 1 is freed after cooling by mechanically destroying the embedding substance. After removal of ridges and projecting material, the substitute is treated with a sandblast blower, preferably with very fine corundum, so that the pores in the outer layer are opened.

Instead of the two-part cuvette shown in FIGS. 2 to 11 it is naturally also possible to use a single cuvette, which is initially only partly filled, preferably to about two thirds, with the embedding substance in which, using a model, a negative mold is made. According to a variant of the preceding method which is especially suitable for the preparation of prefabricated implants of the same shape, a platinum mold is used. The cavity of the platinum mold corresponds to the outer contour of the implant. The shell mold is used instead of the negative mold prepared according to FIG. 2 to FIG. 4; the procedural steps carried out in FIG. 5 to 11 correspond to those previously described.

The above-described procedure can be varied in that a heap of special ceramic material such as is used for the outer layer 6 is applied on the mold filled with ceramic substances before the embedding substance 16 is applied. This heap can also consist of ceramic substances melting between 850° and 1000° C., which contain an admixture of carbon granules, preferably 5 to 20 wt. %. On sintering, this heaping effects consolidation of the material in the mold 14 due to a large increase in volume.

For the preparation of dental root substitutes or artificial teeth pertaining to the original, a negative also true to the original is required, from which the dental root substitute or artificial tooth can be completed. The negative must be composed of an embedding substance which if possible has only a small thermal ability to expand. This shouldn't be greater than 1%. The negative is made according to the invention as follows:

Before extracting the tooth or the dental root a complete impression of the jaw is made. This is followed by extraction of the tooth or the dental root. After correction of the gum edges, protruding gum being trimmed and flaps being cleared away, and where necessary after deepening the tooth recess by means of a bone cutter (mill), or a so-called "Rosenbohrer" or drill, and stopping the blood flow using a vessel-constricting substance, an elastic gum impression material is pressed into the tooth recess. By now applying the complete jaw impression which likewise in the region of the extracted tooth is filled with impression material, a "tooth or root positive" can in this way be obtained. After making plaster of Paris models the tooth positive which reproduces the root recess and the original crown true to shape can be built up to completion in the crown region according to the optimal gnathologic shape.

I claim:

1. Method for the preparation of implants from ceramic substances, especially with a porous surface stimulating the ingrowth of bone tissues, comprising: introducing a model of the implant into a high-temperature embedding substance which has been mixed to a paste and leaving it in this until the embedding substance hardens thus producing a negative mold of the implant removing the model from the mold and lining the mold via an opening reaching into its interior with a layer of a ceramic substance which should form the outer layer of the implant, subsequently completely filling the cavity of the mold with dentine or core substances, sealing the opening with a high-temperature embedding substance which is mixed to a paste, drying the embedding substance, and heating the product to the sintering temperature of the ceramic substance used, and firing the ceramic substances at this temperature.

2. Method for the preparation of implants according to claim 1, wherein the embedding substance is embedded in a muffle or cuvette which is free of scale.

3. Method for the preparation of implants according to claim 2, wherein the muffle is filled at first to about two thirds with the embedding substance previously stirred to a paste, the model subsequently pushed into the embedding substance from above, and that after filling the negative mold with the ceramic substances the rest of the muffle is filled up with embedding substance.

4. Method for the preparation of implants according to claim 1, wherein the negative mold is prepared using a wax model of the implant which is burned out after the embedding substance has hardened.

5. Method for the preparation of implants from ceramic substances, especially with a porous surface stimulating the ingrowth of bone tissues, comprising: lining a shell mold corresponding to the shape of the implant via an opening reaching into the interior of said shell mold with a layer of a ceramic substance which should form the outer layer of the implant, subsequently completely filling the shell mold with dentine or core substances, sealing the opening with a high-temperature embedding substance mixed to a paste, hardening said embedding substance, heating the product to the sintering temperature of the ceramic substances used, and firing the ceramic substances at this temperature, said shell mold being formed of a noble metal alloy which is not destroyed at the firing temperatures of approximately 1000° to 1500° C.

6. Method according to claim 3, wherein a shell mold of a temperature-stable noble metal alloy, preferably a platinum mold, is used.

7. Method for the preparation of implants according to claim 1, wherein the outer layer is formed of a ceramic substance having thin inorganic fibers mixed therein, said fibers having a melting point higher than said sintering temperature, said ceramic substance containing a plurality of vacuoles formed therein for allowing ingrowth of bone tissue.

8. Method for the preparation of implants according to claim 7, wherein the outer layer of the implant is applied to a thickness of about 0.1 to 5 mm, preferably about 0.3 to about 1 mm, and prefired, prior to filling up the rest of the space in the mold or shell mold with a dentine or core substance.

9. Method for the preparation of implants according to claim 1, wherein, before covering the opening leading to the interior of the mold or shell mold with embedding substance which has been mixed to a paste, a metal or hard ceramic insert is introduced into the interior of said mold or shell mold, the insert being preferably an aluminum oxide tube or pin which protrudes above the mold.

10. Method for the preparation of implants according to claim 7, wherein an addition of substances stimulating bone formation and/or bone growth, especially tri-calcium phosphate and tertiary calcium phosphate, is made to the ceramic substances forming the outer layer of the implant.

11. Method for the preparation of implants according to claim 10, wherein the substances stimulating bone growth contain apatite crystals in powder form, preferably calcium phosphate hydroxyl apatite, in quantities of about 5 to 70 wt. %, preferably about 10 to 30 wt. % relative to the dry content of the corresponding ceramic substances.

* * * * *